United States Patent [19]

Cashaw et al.

[11] Patent Number: 4,705,712
[45] Date of Patent: Nov. 10, 1987

[54] OPERATING ROOM GOWN AND DRAPE FABRIC WITH IMPROVED REPELLENT PROPERTIES

[75] Inventors: Alan G. Cashaw; Robert Cole, both of North Brunswick; Rory Holmes, Princeton; Herbert L. Whitaker, Jr., Lebanon, all of N.J.; Lauren Jackson, San Clemente, Calif.

[73] Assignee: Chicopee Corporation, New Brunswick, N.J.

[21] Appl. No.: 895,568

[22] Filed: Aug. 11, 1986

[51] Int. Cl.⁴ .................................................. B32B 5/06
[52] U.S. Cl. .................................... 428/152; 427/206; 428/172; 428/283; 428/284; 428/286; 428/287; 428/288; 428/299; 428/326; 428/903

[58] Field of Search ............... 428/283, 152, 284, 172, 428/286, 287, 288, 299, 326, 903; 26/51; 28/103, 240, 247; 427/206

[56] References Cited

U.S. PATENT DOCUMENTS 4,501,792  2/1985  Holmes et al. ...................... 428/299

Primary Examiner—Marion C. McCamish

[57] ABSTRACT

A repellent, breathable, non-woven fabric is described, having improved repellent properties, one surface of said fabric being corrugated in the machine direction and comprising entangled cellulosic fibers and loosely entangled polymeric fibers, said corrugated surface comprising predominantly entangled cellulosic fibers, said fabric having been additionally coated with fine fibers on the corrugated surface.

21 Claims, 4 Drawing Figures

OPERATING ROOM GOWN AND DRAPE FABRIC WITH IMPROVED REPELLENT PROPERTIES

This invention relates to a repellent, breathable, nonwoven fabric having improved repellent properties. The fabric is corrugated in the machine direction and comprises entangled cellulosic fibers and loosely entangled polymeric fibers, the corrugated surface comprising predominately entangled cellulosic fibers, the fabric having been additionally coated with fine fibers on the corrugated surface. The invention also relates to a method for preparing the coated fabric. The fabric is especially useful for operating room gowns and drapes.

BACKGROUND OF THE INVENTION

Many fabrics have been developed in the past for use as disposable operating room gowns, surgical drapes and wraps for medical components. These fabrics which must be fluid repellent and themselves sterilizable are used to maintain sterility by providing a barrier to contamination; and in the case of fabrics used for operating gowns, it is important that the fabric is breathable and possess sufficient drape for comfort. U.S. Pat. No. 4,501,792 discloses a breathable, repellent, soft fabric with enhanced drape and enhanced frictional properties. This fabric comprises cellulosic fibers and polymeric fibers, the fabric comprising rudimentary discontinuous rows of entangled cellulosic fibers alternating with rudimentary discontinuous rows of loosely entangled polymer fibers, the rows extending in the machine direction and the fabric having a surface comprising predominately entangled cellulosic fibers and a surface comprising predominately entangled polymeric fibers, at least the cellulosic fibers being subject to a repellent treatment. The repellency of the gown of U.S. Pat. No. 4,501,792 is accomplished by finishing the fabric with a suitable repellent such as a fluorochemical. The fluorochemical molecules interact with the pulp layer of the fabric and subsequent high temperature curing allows the fluorochemical "tails" to orient themselves away from the pulp fiber to produce a low surface energy barrier to aqueous fluids. However, the porosity of the base substrate is a primary factor in achieving a superior degree of repellency. The more porous the substrate is, the more the repellency rate decreases (even if finished with a superior fluorochemical treatment). The fabric of U.S. Pat. No. 4,501,792 is composed of a core of entangled polymer, preferably polyester, which is about 40% by weight, with a pulp tissue layer that is about 60% by weight entangled into the polyester core. The top pulp layer of the fabric of U.S. Pat. No. 4,501,792 is composed of individual pulp fibers and fines that are intermeshed and held together mainly by hydrogen bonding. The entangling process by means of which said fabric is made leaves the fabric with certain pulp-poor areas as well as with fine holes. Aqueous fluids penetrate the fabric more readily at the defect sites than at the areas where the pulp layer is dense and uniform. Accordingly, the fabric of U.S. Pat. No. 4,501,792 possess a rather high air-porosity and thus a relatively low repellency rating. In accordance with the present invention, there is provided a method which improves said repellency rating.

Defensive Publication No. 17060 discloses a two-sided laminar fabric formed by uniting a web of synthetic fibers with paper sheet by mechanical entangling, fluid entanglement and/or bonding. A DuPont fabric sold under the name "Fabric 450 TM" comprises an entangled fabric of polymeric and wood pulp fibers containing alternating rows of wood pulp and polymeric fibers with a thin veneer of wood pulp on one surface thereof. The coating process of the present invention may be utilized in order to improve the repellency rating thereof.

The present invention describes the improvement of repellent properties by reducing the porosity of a nonwoven base fabric by depositing a second layer of pulp onto the surface of the fabric utilizing a dilute pulp/water slurry. The second ply of pulp which is applied onto the pulp side of the fabric serves to fill in the holes in the pulp-poor areas that were created during the entangling process. The repellent properties of the two-ply pulp fabric improves hydrostatic head, drop test and impact spray rating in comparison to a similar untreated fabric.

Although the technology producing a pulp sheet by applying multiple layers of pulp on top of each other has existed in the paper making industry for many years, the present concept of forming a second layer, or multiple layers of pulp on the surface of an entangled nonwoven fabric has not been taught in the art.

A number of patents disclose processes for making pulp coated fabrics by depositing a thin layer or coating of wet paper pulp onto and into various fabrics in such a way that the paper pulp becomes a permanent and substantially integral part of the finished material. An example thereof is U.S. Pat. No. 1,854,414. Other patents relating to similar subject matter are U.S. Pat. No. 3,661,700; U.S. Pat. No. 2,913,365; and U.S. Pat. No. 1,782,785. However, none of said patents disclose an inital cross directional stretching of the fabric before the pulp layer is deposited thereon; which step is an essential and unobvious feature of the present invention. This initial cross-stretching step brings bout an expansion of the pores of the fabric which would be expected by a skilled person, to actually reduce the internal bond of the fabric. It has been found, however, in accordance with the present invention, that this cross-stretching step very surprisingly improves the Internal Bond of the resultant fabric as compared to unstretched fabric coated in the same manner.

SUMMARY OF THE INVENTION

The present invention comprises a repellent breathable, nonwoven fabric, having improved repellent properties. The fabric surface is corrugated in the machine direction and comprises entangled cellulosic fibers and loosely entangled polymeric fibers, the corrugated surface comprising predominantly entangled cellulosic fibers. The fabric is covered with a coating of fine fibers on the corrugated surface, the Internal Bond, according to the TAPPI Test No. J506SU68 being at least 5 Kg/sq. in.

The present invention also relates to a process for preparing said coated fabric. Said process comprises continuously subjecting the fabric to cross-tension so as to cross-stretch the fabric an amount equal to between 5% and about 80% of the unstretched width thereof, the fabric having been initially treated with from 0% to 500% wet pickup, based on the dry weight of the fabric of a fluid containing repellent materials. Thereafter, an aqueous slurry of fine fibers are continuously deposited onto the corrugated surface of the fabric, at least 70% by weight of the fine fibers being capable of passing through a 200 mesh screen with diagonal hole openings of 74 microns, the concentration of fibers in the slurry varying between 0.005% and 10% by weight of the total slurry, whereby a coating of fine fibers is formed on and in the fabric, there being between 0.5% and 10% by weight of the coating, based upon the total weight of the treated fabric, a repellent fluid being optionally included in the aqueous slurry so as to add repellent to the coating. Thereafter, a portion of the water is removed from the coated fabric while the later is preferably still in cross-stretched condition. The cross tension is then released and the coated fabric is dried and any repellent therein is cured.

The resultant fabric possesses the following properties:

the Hydrostatic Head according to AATCC Test No. 127-1974 is at least 30 cms;

the Internal Bond, according to the TAPPI Test No. J506SU68 is at least 5 Km/sq. in.; and the Hand, according to the TAPPI Test No. T498 is less than 50 grams.

The Spray Impact is less than 1 gm.

The resultant fabric possesses an improved repellency rating as compared to the untreated fabric. The resultant fabric also possesses all of the properties of the untreated fabric such as its softness, drape, enhanced frictional properties and tensile strength in the machine direction (as disclosed in the prior art drape of U.S. Pat. No. 4,501,792).

DETAILED DESCRIPTION OF THE INVENTION

Figure 2:
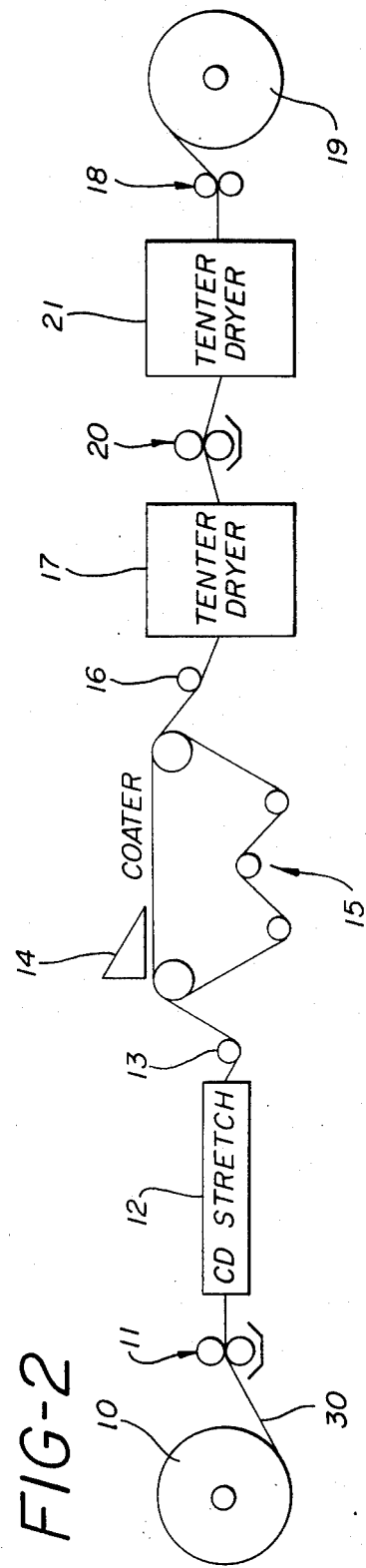
FIG. 2 is a schematic side elevation of an apparatus suitable for carrying out a further modification of the process of the invention.

The preferred gown fabric, utilized in accordance with the present invention is that shown in FIG. 2 of U.S. Pat. No. 4,501,792, which is incorporated herein by reference. This fabric comprises rudimentary discontinuous rows of entangled cellulosic fibers alternating with rudimentary discontinuous rows of loosely entangled polymeric fibers, the rows extending in the machine direction and the fabric having a surface comprising predominantly entangled cellulosic fibers and an opposite surface comprising predominantly entangled polymeric fibers.

Figure 3:
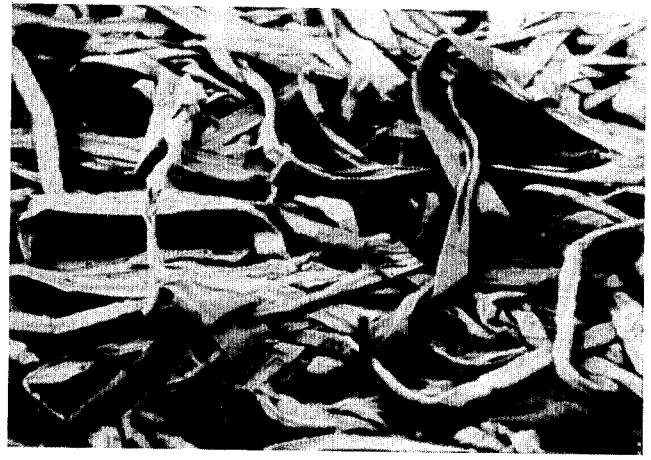
FIG. 3 is a 200 X photomicrograph of a plan view of the pulp layer of the prior art fabric of U.S. Pat. No. 4,501,792.
Figure 4:
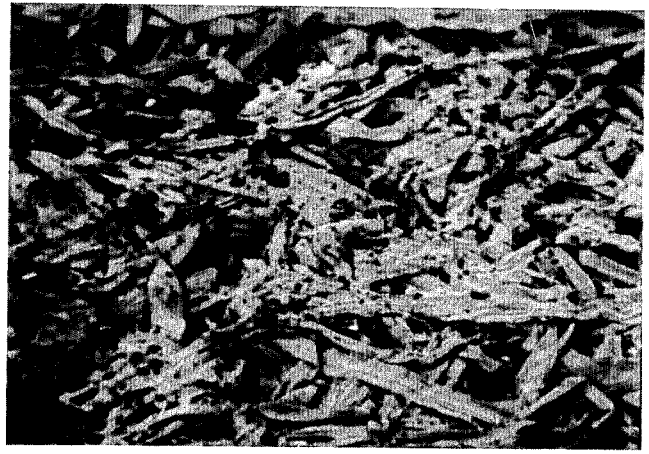
FIG. 4 is a 200 X photomicrograph of the same surface as shown in FIG. 3 after having been coated according to the present invention.

The standard fabric of the reference is composed of a core of entangled polyester, with a pulp tissue layer entangled into the polyester core. The top pulp layer is composed of individual pulp fibers and fines that are intermeshed and held together mainly by hydrogen bonding. The entangling process leaves the standard fabric with pulp-poor areas as well as with fine holes. Aqueous fluids therefore penetrate the fabric more readily at the defect sites than at the areas where the pulp layer is dense and uniform. FIG. 3 of the present drawings shows a surface photomicrograph of the standard fabric, demonstrating the individual pulp fibers and fines in the pulp tissue layer. Present FIG. 4 demonstrates the standard reference fabric after it is has been treated in accordance with the present invention. The treated fabric consists of a two-ply pulp layer and has a more dense and uniform surface structure. It will be noted that the second layer of pulp has filled in many of the fine holes and pulp-poor areas.

Figure 1:
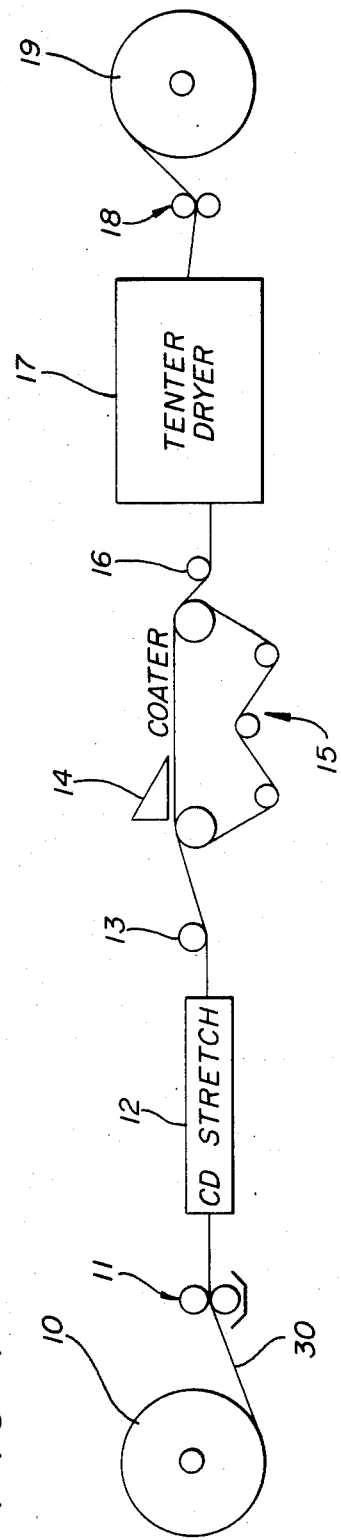
FIG. 1 is a schematic side elevation of an apparatus suitable for carrying out a preferred process of the invention as well as modifications thereof.

The standard reference fabric (known as standard EFP Fabric) is preferably treated utilizing the appartus shown in FIG. 1 of the present drawings. Thus, in accordance with a preferred process of the present invention, standard gown fabric of EFP is first unwound from the unwind stand 10 shown in FIG. 1. This fabric is saturated with repellent finish in the padder 11. Examples of suitable water repellent finishes are wax emulsions, polyurethane emulsions, silicones and fluorochemicals, the latter constituting the preferred repellent. Examples of suitable repellent finishes which may be utilized in accordance with the present invention are: Aerotex 96B, sold by American Cyanamic (which comprises a polyurethane emulsion); Phobotex, sold by Ciba-Geigy (consisting of a wax emulsion); FC 826, sold by Minnesota Mining and Manfucaturing (consisting of a fluorochemical); and Milease F-14 and Milease F-31X, sold by ICI, (consisting of a fluorochemical).

The following is a listing of other suitable repellent finish raw materials, plus two examples of formulations:

| Fluorocarbon | Extenders |
| --- | --- |
| (Fluorinated Polyacrylates | |
| 3M FC-824 | Hyad HFW (which is polyurethane based), sold by Sandoz Chemical |
| 3M FC-831 | Astropel (which is a melamine wax), sold by Astro Industries |
| 3M FC-838 | Phobotex (which is a high molecular weight melamine wax), sold by Ciba-Geigy |

Examples of Repellent Finishes Suitable for Untreated Fabric of the Present Invention, known as Sahara 1. Four parts by liquid weight of Astropel to one part by liquid weight of FC-824, pH between 5 and 6, mixed into solution at 2% dry solids by weight of water.
2. Three parts of Hyad HFW to 1 part of 3M FC-831, pH between 5 and 6, in a solution of 2% by weight of water.

The above repellent finishes, which improve the repellency of the fabric are applied in the range of between 0.05% and 25% by weight of the untreated fabric, the preferred range being between about 0.2% and 0.25% by weight based upon the weight of the treated fabric.

Although it is not essential, it is most preferred to add the repellent prior to the stretching step. This is due to the fact that the repellent is lubricious so that the fabric is more easily stretched after such repellent treatment.

After the repellent is added, the EFP fabric is transferred to a CD stretch frame 12 and stretched to between 5% and about 80% of the unstretched width thereof in the cross direction (although the preferred stretch is about 40%). One advantage of the initial stretching step lies inthe fact that after the coating is applied to the fabric, the latter is allowed to shrink bringing about a non-planar surface. The resultant enhanced frictional properties of the fabric improve its characteristics as a wrap for medical components in that the wrap is not easily dislodged and does not easily come unwrapped. Further, when used as a surgical drape, the enhanced frictional properties provide a drape which will more easily stay where it is initially placed and provides a non-slip gripping surface for surgical instruments and the like disposed on the drape.

After, the stretched fabric is transferred to a secondary head box Fourdrinier system 14 where it is coated with an aqueous slurry of fine fibers, at least 70% by weight of the fine fibers being capable of passing through a 200 mesh screen, the concentration of fibers in the slurry varying being 0.05% and 10% by weight of the total slurry. A coating of fine fibers is thus formed on and in the fabric, there being between about 0.5% and 10% by weight of the coating, based upon the total weight of the treated fabric. The slurry preferably consists of a mixture of cellulose acetate and softwood pulp. The slurry also has added thereto, sufficient repellent so that substantially the same percentage by weight of repellent is eventually deposited on the fiber coating based on the weight of the coating, as was initially added to the fabric in the padder 11. Although the preferred method of depositing the fine fibers on the fabric consists of the use of a slurry and a Fourdrinier head box, the fibers may also suitably be deposited on the fabric by means of sprays, weirs, metered flow applicators or electrostatic particle applicators.

The non-aqueous portion of the slurry preferably comprises (i) filler material comprising refined pulp 70 to 100 microns in length and 25-35 microns in diameter and (ii) networking material which comprises microfibrillated fibers having a length of from 50 to 70 microns and having an average diameter of from 1 to 5 microns and (iii) a bonding agent (preferably a polyamine) and (iv) the repellent, the ratio of filler material to networking material varying between 90:10 and 10:90. The preferred weight ratio of filler material to net working material to bonding material is 3:1:1.

In accordance with a preferred method of the presently claimed process, the treated fabric is dewatered in the Fourdrinier while still in a stretched condition. In this way, it is easier for the water to pass through the pores in the fabric. After treatment, the fabric is preferably allowed to contract between about 1.0% and 10%. This results in a crinkled non-planar surface which is especially useful for use in making repellent breathable drapes and gowns for use in a sterile environment.

Preferably, sufficient water is added to the padder 11 so that the fabric leaves the CD stretch frame 12 having a solid content of between 40% to 50%. After the coating step in the Fourdrinier system 15, the coated fabric is brought down to a level of approximately 30% solids by an air suction and then transported to the tenter drier 17 wherein the fabric experiences evaporative drying with control (via tentering) down to 100% solids and 0% moisture. The fabric is then passed through the calendar nip 18 and thereafter it is wound on the windup 19. The treated fabric prepared in accordance with the above discussed preferred method is suitable for operating room gown fabric. It has a repellency of greater than 30 cm. of hydrostatic head. It will repel alcohol, oil and surfactant drops for 15 minutes or greater from the pulp side. It will demonstrate textile strengths from 25 to 30 lbs. in the machine direction for 4" grabs and from 16 to 22 lbs. in the cross direction with the same 4" grab. It will emulate bursts between 45 and 53 lbs. It will have drape characteristics that read on a Thwing-Albert Handle-O-Meter between 27 and 40 grams in the machine direction.

A modification of the above process, utilizing the apparatus of FIG. 1, is carried out as follows:

Standard EFP fabric is unwound from the unwind 10. The fabric is then saturated with water only in the padder 11. Thereafter the gown is stretched in the CD stretch 12, preferably about 25% in the cross direction. The stretched fabric is then transferred to the Fourdrinier secondary headbox coating station 15 wherein a coating of cellulose acetate and softwood pulp is deposited from the headbox 14 onto the fabric. The slurry utilized in this connection contains sufficient repellent so that the desired amount of repellent is deposited on both the fabric and the coating so as to bring about the desired concentration of repellent. The fabric is initially delivered to the Fourdrinier station 15 containing between 40% and 50% solids; and it is transferred from the Fourdrinier station 15 containing about 30% solids. Thereafter the fabric is dried in the tenter dryer 17, passed through the calendar nip 18 and would on the windup 19.

A further modification of the process of the present invention is described with reference to FIG. 2 of the drawings as follows:

The EFP fabric 30 is unwound from the unwind 10 and passed through the padder 11 in order to saturate said fabric in a pad bath of water or surfactant.

Fabric 30 is then stretched in the cross direction approximately 25% of its width in the CD stretch 12. Thereafter the stretched fabric is transferred to the Fourdrinier 15 and coated preferably with a coating of cellulose acetate and softwood pulp, there being no repellent in the slurry emerging from headbox 14. (However, in accordance with yet another modification of the process of the present invention, repellent is, indeed, optionally included in the slurry emerging from the headbox 14, as well as in the padder 20 as subsequently described). As was the case with the previously discussed processes, the fabric 30 is received at the Fourdrinier station 15 containing from 40 to 50% solids; and the fabric 30 leaves the Fourdrinier station 15 containing approximately 30% solids. Thereafter, the coated fabric is dried by means of drying cans or a tenter oven 17 which controls the cross direction tension.

The dried fabric is then passed into a padder 20 which contains the desired amount of repellent finish. The fabric 30 is then again dried in a tenter drier and thereafter subjected to a nipping in calender nip 18. The dip and nipping will result in a finish pick up of approximately 20 grains per square yard but which may vary as low as 6 grains per square yard and be as high as 100 grains per square yard. Thereafter, the treated fabric is wound on the windup 19. The properties thereof are similar to those of the fabrics prepared by means of the alternative processes described hereinabove.

The coating of fine fibers utilized in accordance with the present invention is preferably produced from a mixture of cellulose acette and softwood pulp known by the trademark "Solka Floc". A 50/50 blend thereof has been found to be most suitable. The use of more Solka Floc in the coating to increase the mixture ratio causes the adhesion properties of the coating to decline. This coating is easily dyed so as to cause minimal deviation from specified color values. Furthermore, test results have indicated that as the coating weight has been increased, the hydrostatic head has also increased. At a coating weight level of 50 grains per square yard, a hydrostatic head of 49 cm. was achieved. However, delamination of the coating from the base fabric begins to occur at about the 50 grain per square yard coating weight level. Other suitble fine fibers which may be utilized in accordance with the present invention are as follows:
1. Microfibrillated Cellulose Acetate.
2. Microfibrillated Cellulose
3. Microfibrillated Cellulose collected by the effluent stream in the entangled fiber (EF) process
4. Highly Refined Softwood Cellulose
5. Solka Floc (which is highly refined soft and hardwood pulp)
6. Cellufloc (which is highly refined soft and hardwood pulp)
7. Acetobacter xylinum (which is microfibrilated fibers produced by one cell organisms)

| Organic and Inorganic Filler Materials | |
|---|---|
| Organic | Inorganic |
| Eastobond (micropellets of polyethylene) | $T_1O_2$ |
| Carboxymethylcellulose | $CaCO_3$ |
| Starch, etc. | Salts, etc. |

The weight of the coating can range from 5 grains per square yard to 100 grains per square yards, the hydrostatic head measurement increasing as the coating weight increases. However, heavy coating weights can cause delaminatio from the base fabric under slight stress. The ratio of pulp and non-pulp species within the coating may be widely varied and depends upon the desired characteristics of the fabric.

The following are descriptions of certain standard tests carried out herein:

Water Resistance: Impact Penetration Test (AATCC Test Method 42-1980).

The method of this test is applicable to any textile fabric, which may or may not have been given a water resistance or water-repellent finish. It measures the resistance of fabrics to the penetration of water by impact. The results obtained with this test depend on the water repellency of the fibers and yarns and on the construction of the fabric. In accordance with this test, water is allowed to spray from a height of two feet against the taut surface of a test specimen backed by a weighed blotter. The blotter is then reweighed to determine water penetration and the specimen is classified accordingly.

Water Repellency: Spray Test

In accordance with this test, water is sprayed against the taut surface of a test specimen under controlled conditions to produce a wetted pattern the size of which depends on the relative repellency of the fabric. Evaluation is accomplished by comparing the wetted pattern with pictures on a standard chart.

Hydrostatic Pressure Test AATCC Test No. 127-1974

In accordance with this test, a specimen is subjected to increasing water pressure while the undersurface is observed for leakage.

Abrasion Resistance of Non-Woven Fabrics ASTM Test D-3886

In accordance with this test, a sample is abraded using rotary rubbing action under controlled conditions of pressure and abrasive action. One abrading wheel rubs the speciment outward towards to periphery and the other inward towards the center. The results and damage is noted at a determined number of cycles.

Grab Tensile Strength ASTM Test D-1682

This test applies to the determination of wet and dry tensile strengths of nonwoven fabric. In accordance with this test, Instron grips are separated at a constant rate until the fabric breaks. The force necessary to cause this break is measured.

Hand (softness) of textiles ASTM Test D-1388

This method is applicable to the determination of softness or hand of both woven and nonwoven fabrics. The method employs a Handel-O-Meter to measure the flexural resistance generated when bending the fabric.

Mullen Burst Testing of Nonwoven Fabrics ASTM Test D-3786

Bursting strength is defined as the pressure in pounds per square inch required to produce rupture of the material when this pressure is applied at a controlled increasing rate through a rubber diaphragm to a circular area of the sample.

Repellency of Disposable Fabrics Liquid Holdout (Drop Test)

This method is applicable to the determination of the repellency of certain nonwoven fabrics. Low surface tension test fluids are placed by drops on the surface of the fabric to be tested. The ability of the fabric to prevent penetration of these fluids is rated by comparison with visual standards.

Internal Bond Value Test TAPPI Test T506 SU 68

This test is a measure of the extend of 3-dimensional entanglement. It is believed that this test measures the ability of the fibers that penetrate the entangled fiber regions at substantial angles to the plane of the fabric to prevent delamination in the test.

An example of the preparation of the coated fabric of the present invention is as follows. This example is not intended to be limiting in any way and extentions and modifications thereof, without departure from the spirit and scope of the invention, will become apparent from the example.

The following is a listing of suitable processing equipment for carrying out the following Example:
1. An Egan spindle unwind stand.
2. A Kuster dip and nip pad saturation station.
3. A Hofstetter tenter (specification: 100" to 180" over 20 feet in Length).
4. A Sandy Hill secondary headbox.
5. A Sandy Hill fourdrinier table (specification: vacuum boxes, breast roll, non-suction couch roll, guide system).
6. A Hofstetter dryer and tenter.
7. A twin-roll surface winder by Egan.
8. The stock preparation section is accomplished via: (a) a Baracuda pulper by Beloit Jones; (b) sprout Waldron double-disk, 36-inch refiner; (c) machine chest by Beloit Jones—agitated; (d) a stock pump by Peerless; (e) a fan pump by Peerless; (f) a whitewater silo by Beloit Jones; (g) a dry seal vacuum pump by Hoffman or Nash; (h) a whitewater tank by Beloit Jones; (i) a belt showering system including a micro-strain by Albany Engineering.

EXAMPLE

A roll of the fabric of the type described in U.S. Pat. No. 4,501,792 is unwound from an unwind stand. The fabric comprises rudimentary discontinuous rows of entangled wood pulp fibers alternating with rudimentary discontinuous rows of loosely entangled polyester fibers, the rows extending in the machine direction and the fabric having a surface comprising predominantly entangled wood pulp fibers and an opposite surface comprising predominantly entangled polyester fibers. The fabric weighs 2.06 ounces per square yard. The fabric is composed of a core of entangled polyester which is 40% by weight with a pulp tissue layer that is 60% by weight entangled into the polyester core. The entangling process by means of which the fabric was produced, tends to leave the fabric with pulp-poor areas as well as with fine holes.

The fabric is then saturated with an aqueous suspension of a fluorocarbon repellent in a padder. The amount of fluorocarbon suspension in the water is approximately 2% by weight of the suspension and the amount of repellent deposited on the fabric is approximately 2% by weight of the fabric. The fabric is simultaneously nipped to a 100% wet pick-up. Thereafter, the fabric is stretched in the cross- direction on a stretch frame so that the cross-direction width is increased by approximately 29%. The resulting stretched fabric weighs approximately 1.6 ounces per square yard.

Thereafter, the stretched material is transferred to a Fourdrinier having a secondary headbox. The fabric is coated with cellulose acetate and softwood pulp. The pulp slurry utilized consists of a 75/25 softwood pulp: cellulose acetate mixture. This mixture has been refined to an average fiber size of about 70 microns. The softwood pulp portion has a fiber diameter of about 25 microns and the cellulose acetate has a fiber diameter of approximately 1 micron. The slurry which is applied also contains 2% by weight of a flurocarbon repellent based upon the weight of the slurry so that the total amount of repellent deposited in the fabric is equal to about 0.07 ounces per square yard thereof. After the coating is applied from the headbox, the coated fabric is drained by means of suction boxes down to 30% solids. Thereafter the coated fabric is transferred to a tenter dryer for evaporative drying. In this tenter dryer, the fabric is dried to 100% solids and 0% moisture. After drying, the fabric is passed over a breaker bar for softening and the resultant fabric is then wound on a windup, being cured and in the finished state.

The finished fabric possesses the following properties:

the hydrosttic head according to the AATCC Test No. 127-1974 is at least 30 cm;

the Internal bond according to the TAPPI Test No. J506SU68 is at least 5 kg. per square inch; and the Hand according to the TAPPI Test No. T498 is less than 50 grams.

The Spray Input is less than 1 gm.

The finished fabric repels alcohol, oil and surfactant drops for 15 minutes or greater from the pulp side. It demonstrates tensile strengths from 25–30 lbs. in the machine direction for 4" grab, and from 16–22 lbs. in the cross direction for the same 4" grab. It emulates bursts between 45 and 53 lbs. The fabric has drape characteristics that read on a Thwing-Albert Handle-O-Meter between 27 and 40 grams in the machine direction.

The treated fabric produced in accordance with the above example, in which the substrate was initially stretched, was compared with an identical treated substrate which was not stretched at any time. It was determined that the stretched substrate possessed an internal bond of 5.8 kg. per square inch whereas the corresponding unstretched substrate only possessed an internal bond of 5.2 kg. per square inch. As pointed out above, this is surprising since the initial cross-stretching step brings about an expansion of the pores of the fabric which would be expected by a skilled person to actually reduce the internal bond thereof as compared to a comparable unstretched fabric coated in the same manner.

Other tests carried out comparing the unstretched with the stretched substrates showed that the repellency values and machine direction tensile strengths of the unstretched material were higher than those of the stretched material. However, this, per se, is to be expected since the unstretched material possesses a considerably greater weight of substrate as well as coating, and on a per ounce basis the stretched fabric is better.

The following is a breakdown of the constituents of the treated fabric of the present invention (known as Sahara) compared to the identical corresponding fabric which has not been treated by Sahara. (Referred to herein as the standard fabric):

TABLE I
SAHARA PROTOTYPE COMPOSITION

| Composition | Sahara | Standard |
|---|---|---|
| Weight Greige Fabric (oz/sq yd) | 2.06 | 2.16 |
| Pulp (%) | 55 | 55 |
| Polyester (%) | 45 | 45 |
| Stretch (%) | 29 | 3.4 |
| Weight Stretched Fabric (oz/sq yd) | 1.6 | 2.07 |
| Finish Formula | Cellulose Acetate/Albacel Softwood Pulp/CGIII | CGII |
| Finish Weight (oz/sq yd) | 0.15 | 0.03 |
| WEIGHT FINISHED FABRIC (oz/sq yd) | 1.75 | 2.1 |

The following is a comparison of Sahara performance properties as compared to the standard gown performance properties:

TABLE II
SAHARA PROTOTYPE COMPOSITION

| Properties | Sahara | Standard |
|---|---|---|
| Weight (oz/sq yd) | 1.75 | 2.1 |
| Hydrostatic Head (cm) | 30 | 22 |
| Spray Impact (grams) | 0.2 | 18 |
| Hand (grams) | 22 | 27 |
| Tensile | | |
| MD (lbs) | 27 | 28 |
| CD (lbs) | 18 | 18 |
| Burst (lbs) | 40 | 40 |
| Drops | | |
| Alcohol | 15 | 5 |
| Oil | 15 | 5 |
| Surfactant | 15 | 5 |
| Internal Bond (kg/in$^2$) | 5 | 15 |

The above tests referred to in Table II were carried out in a static sheet mold. The internal bond, as discussed above, in the static test is 5.8 kg/sq inch (with respect to the stretched material). This compares to an internal bond of 5 kg/sq inch which was obtained from a dynamic test on a continuous sample of the stretch material produced in accordance with the Example. However, in a dynamic test on a continuous sample the internal bonding of the coating would also be less on the unstretched material than on the stretched material. In addition, the drainage rate on the unstretched material would be slower and incumbered by the smaller pore size of the unstretched material, causing lower vertical penetration of the coating fibers, thus causing delamination at low abrasion.

What is claimed is:

1. A repellent, breathable non-woven fabric, said fabric comprising rudimentary discontinuous rows of entangled cellulosic fibers alternating with rudimentary discontinuous rows of loosely entangled polymeric fibers, said rows extending in the machine directio and said fabric having one surface comprising predominantly entangled cellulosic fibers and an opposite surface comprising predominantly entangled polymeric fibers, said fabric having been repellent treated and coated with fine fibers on said one surface, at least 70% by weight of said fine fibers being capable of passing through a 200 mesh screen, there being between 0.5% and 10% by weight of said fiber coating based upon the total weight of said treated fabric; said fabric possessing the following properties:

the Hydrostatic Head according to AATCC Test No. 127-1974 is at least 30 cms;

the Internal Bond according to the TAPPI Test No. J506SU68 is at least 5 Kg/sq. inch; and the Hand, according to the TAPPI Test No. T498 is less than 50 grams.

2. An operating room gown prepared from the fabric of claim 1 wherein said cellulosic fibers comprise wood pulp fibers and said polymeric fibers comprise polyester fibers.

3. A drape prepared from the fabric of claim 1.

4. A process for improving the repellent properties of repellent, breathable, non-woven fabric, one surface of said fabric being corrugated in the machine direction and comprising entangled cellulosic fibers and entangled polymeric fibers, said one surface comprising predominantly entangled cellulosic fibers; said process comprising:

(a) continuously subjecting said fabric to cross-tension so as to cross-stretch said fabric an amount equal to between about 5% and about 80% of the unstretched width thereof, said fabric having been initially treated with from 0% to 0.2% repellent by weight based on the dry weight of the fabric.

(b) continuously depositing an aqueous slurry of fine fibers onto said corrugated surface of said fabric, at least 70% by weight of said fine fibers being capable of passing through a 200 mesh screen with diagonal hole openings of 74 microns, the concentration of fibers in said slurry varying between 0.005% and 10% by weight of the total slurry whereby a coating of fine fibers is formed on and in said fabric, there being between 0.5% and 15% by weight of said coating, based upon the total weight of the treated fabric, a repellent being optionally included in said aqueous slurry so as to add repellent to said coating;

(c) removing a portion of the water from said coated fabric; and (d) drying said coated fabric and curing any repellent therein.

5. The process of claim 4, which comprises adding repellent to said fabric before the latter is cross-stretched in step (a), the amount of repellent comprising between about 0.05% and 25% by weight of the untreated fabric; and adding sufficient repellent to the slurry in step (b) so that substantially the same percentage amount by weight of repellent is eventually deposited on said fiber coating, based on the weight of said coating, as was initially added to said fabric prior to cross-stretching in step (a);

the water being removed in step (c) by vacuum extraction through the fabric so that fine fibers fill the pores as well as any defect sites in said fabric and thus improve the hydrostatic head thereof.

6. A modification of the process of claim 4, which comprises adding no repellent but rather a non-repellent aqueous solution to said fabric before the latter is cross-stretched in step (a); adding no repellent to the slurry in step (b); and adding repellent, in aqueous suspension to the dired fabric subsequent to step (d) so as to ultimately deposit between about 0.05% and 25% by weight of said repellent on said fiber coated fabric based upon the total weight of the fabric plus fiber coating; and again drying said repellent treated fiber coated fabric and curing the repellent therein.

7. A modification of the process of claim 4, which comprises adding no repellent but rather a non-repellent aqueous solution to said fabric before the latter is cross-stretched in step (a); adding repellent to the slurry in step (b); adding additional repellent after step (d), the total amount of repellent added being such that there is deposited between about 0.05% and 25% by weight of said repellent on said fiber coated fabric based upon the total weight of the fabric plus fiber coating; and again drying said repellent treated fiber coated fabric and curing the repellent therein.

8. A modification of the process of claim 4, which comprises adding no repellent, but rather a non-repellent aqueous solution to said fabric before the latter is cross-stretched in step (a);

and adding repellent to the slurry in step (b) so as to ultimately deposit between about 0.05% and 25% by weight of said repellent on said fiber coated fabric based upon the total weight of the fabric plus fiber coating.

9. The process of claim 4, wherein said fabric comprises rudimentary discontinuous rows of entangled cellulosic fibers alternating with rudimentary discontinuous rows of loosely entangled polymeric fibers, said rows extending in the machine direction, and said fabric having a surface comprising predominantly entangled cellulosic fibers and an opposite surface comprising predominantly entangled polymeric fibers.

10. The process of claim 9, in which said fabric is subjected in step (a) to between 20% and 35% cross-stretching; at least 70% of said fine fibers deposited in step (b) being microfibrillated, the concentration of said fibers in said slurry varying between 0.06 and 0.15% by weight of the total slurry, there being between 2% and 6% by weight of said coating of fibers which is formed on said fabric.

11. The process of claim 10, in which the amount of the repellent comprises between about 2% and 2.5% by weight based upon the weight of the untreatd fabric.

12. The process of claim 10, in which the non-aqueous portion of said slurry in step (b) comprises (i) filler material comprising refined pulp 70 to 100 microns in length and 25 to 35 microns in diameter, (ii) networking material which comprises microfibrillated fibers having a length of from 50 to 70 microns and having an average diameter of from 1 to 5 microns, (iii) a bonding agent and (iv) said repellent, the ratio of filler material to networking material varying between 90:10 and 10:90.

13. The process of claim 12, in which the weight ratio of filler material to networking material to bonding material is 3:1:1, said bonding material being a polyamine.

14. The process of claim 9, in which the fibers in said slurry in step (b) are selected from the group consisting of microfibrillated cellulose, and Cellufloc P.B.-55.

15. The process of claim 4, in which said slurry is deposited on said fabric in step (b) by means of sprays, weirs, headboxes, metered flow applicators or electrostatic particle applicators.

16. The process of claim 4, in which said repellent is a flurochemical, said cellulosic fibers in said fabric comprise wood pulp fibers and said polymeric fibers comprise polyester fibers.

17. The process of claim 16, wherein said polyester fibers in said fabric comprise about 40% by weight of said fabric and said wood pulp fibers comrpise about 60% by weight of said fabric.

18. The process of claim 4, in which said slurry is prepared from a mixture of cellulose acetate fiber and softwood pulp.

19. A repellent, breathable nonwoven fabric, one surface of said fabric being corrugated in the machine direction and comprising entangled cellulosic fibers and loosely entangled polymeric fibers, said corrugated surface comprising predominantly entangled cellulosic fibers, said fabric having been treated with a coating of fine fibers on said corrugated surface according to the process claimed in claim 4, the Internal Bond according to the TAPPI Test No. J506SU68 being at least 5 Kg/square inch.

20. An operating gown, prepared from the fabric of claim 19.

21. A drape, prepared from the fabric of claim 19.

* * * * *

UNITED STATES PATENT AND TRADEMARK OFFICE
CERTIFICATE OF CORRECTION

PATENT NO. : 4,705,712
DATED : November 10, 1987
INVENTOR(S) : Alan G. Cashaw et al.

It is certified that error appears in the above-identified patent and that said Letters Patent is hereby corrected as shown below:

Col. 11, line 8: "directio" should be --direction--.

Col. 12, line 12: "dired" should be --dried--.

Col. 12, line 57: "untreatd" should be --untreated--.

Col. 13, line 16: "comrpise" should be --comprise--.

Signed and Sealed this

Twenty-sixth Day of July, 1988

Attest:

DONALD J. QUIGG

Attesting Officer

Commissioner of Patents and Trademarks